(12) United States Patent
Klein-Kassab

(10) Patent No.: US 10,568,374 B2
(45) Date of Patent: Feb. 25, 2020

(54) MAGNETIC CLOSURE SYSTEM

(71) Applicant: Cooper F. Klein-Kassab, Ann Arbor, MI (US)

(72) Inventor: Cooper F. Klein-Kassab, Ann Arbor, MI (US)

(\*) Notice: Subject to any disclaimer, the term of this patent is extended or adjusted under 35 U.S.C. 154(b) by 0 days.

(21) Appl. No.: 16/270,342

(22) Filed: Feb. 7, 2019

(65) Prior Publication Data

US 2019/0239587 A1 Aug. 8, 2019

Related U.S. Application Data

(60) Provisional application No. 62/628,262, filed on Feb. 8, 2018.

(51) Int. Cl.

| *A41F 1/00* | (2006.01) |
|---|---|
| *A44B 19/26* | (2006.01) |
| *A44B 19/16* | (2006.01) |
| *A45C 13/10* | (2006.01) |
| *H01F 7/02* | (2006.01) |

(52) U.S. Cl.
CPC ............ *A41F 1/002* (2013.01); *A44B 19/267* (2013.01); *A44B 19/16* (2013.01); *A44D 2203/00* (2013.01); *A45C 13/1069* (2013.01); *H01F 7/0263* (2013.01); *Y10T 24/25* (2015.01); *Y10T 24/32* (2015.01)

(58) Field of Classification Search
CPC ......... Y10T 24/32; Y10T 24/24; Y10T 24/25; Y10T 24/26; Y10T 24/45162; Y10T 24/45152; Y10T 24/45157; A44B 19/267; A44B 19/16; A41F 1/002; A45C 13/1069; H01F 7/0263; A44D 2203/00
See application file for complete search history.

(56) References Cited

U.S. PATENT DOCUMENTS

| 3,102,314 | A | * | 9/1963 | Alderfer | ................. | A41F 1/002 24/303 |
|---|---|---|---|---|---|---|
| 3,161,932 | A | * | 12/1964 | Russell | .................... | A41F 1/002 24/303 |
| 4,197,618 | A | * | 4/1980 | Bourguignon | .......... | A41F 1/002 24/303 |
| 6,301,754 | B1 | * | 10/2001 | Grunberger | ............. | A41F 1/002 24/303 |
| 9,721,712 | B2 | * | 8/2017 | Provencher | ........... | H01F 7/0263 |
| 2006/0112523 | A1 | * | 6/2006 | Deto | ....................... | A41F 1/002 24/303 |
| 2007/0277353 | A1 | * | 12/2007 | Kondo | .................... | A41F 1/002 24/403 |

\* cited by examiner

*Primary Examiner* — Robert Sandy
*Assistant Examiner* — Michael S Lee
(74) *Attorney, Agent, or Firm* — John G. Posa; Belzer PC

(57) ABSTRACT

A magnetic closure system includes first and second opposing bodies with permanent magnets disposed on or in sloping surfaces of the bodies to keep the bodies in contact until being pulled apart. The bodies may be rigid, semi-rigid or flexible strips or elongated structures comprised of separate blocks, each block having two divergent sloping surfaces. Whether in strip or block form, each body may be adapted for attachment to a flexible material or fabric, such that the opposing bodies form a magnetic zipper. The magnetic closure system many be used in conjunction with many products, including clothing, curtains, bags, backpacks, purses, mats, tiles, or any other situation wherein materials or fabrics are joined.

21 Claims, 6 Drawing Sheets

MAGNETIC CLOSURE SYSTEM

REFERENCE TO RELATED APPLICATIONS

This application claims priority to, and the benefit of, U.S. Provisional Patent Application Ser. No. 62/628,262, filed Feb. 8, 2018, the entire content of which is incorporated herein by reference.

FIELD OF THE INVENTION

This invention relates generally to zippers and closure structures and, in particular, to a closure system and method that used permanent magnets disposed on or in repeating geometric shapes.

BACKGROUND OF THE INVENTION

Zippers present problems for many people on a daily basis. Getting dressed can be challenging and time-consuming. In many cases the zipper is difficult to latch at the base so that the teeth of the zipper align properly and the slider frequently gets stuck moving up or down. The slider that moves up and down often snags on the cloth around the zipper. As such, available zippers present a real challenge for many people, especially children, senior citizens, those with arthritis, and people who are physically disabled.

SUMMARY OF THE INVENTION

This invention resides in a magnetic closure system finding applicability in many products, including clothing, curtains, bags, backpacks, purses, mats, tiles, or any other situation wherein materials or fabrics are edge-joined. Indeed, the magnetic closure systems disclosed herein have unlimited potential as they may be applied universally for all types of material.

The preferred embodiments are directed to an apparel closure system that minimizes or eliminates existing problems and simplifies the task of getting dressed. Using the inventive magnet closure systems described herein, edges of clothing may be connected and disconnected easily and quickly, while being secure enough to remain attached during normal wear and tear. There is no need for a slider device to "zip" up or down. The simplicity of the magnetic closure system minimizes the amount of effort it takes to attach and detach two pieces of fabric.

A magnetic closure system according to the invention includes first and second opposing bodies, each with a side profile having peaks, troughs and sloping surfaces between the peaks and troughs. Permanent magnets are disposed on or in the sloping surfaces of the bodies, with the poles of the magnets facing outwardly. When the peaks of each body are received by the troughs of the other body, the magnets of one body are attracted to the magnets of the other body to keep the bodies in contact until the bodies are manually pulled apart.

The peaks, troughs and sloping surfaces may be flat, such that the profile of each body defines a repeating trapezoidal pattern or "waveform." Alternatively, the peaks and troughs may be pointed, such that the profile of each body defines a repeating triangular pattern. As a further alternative, the peaks, troughs and sloping surfaces may be curved and smooth, such that the profile of each body defines a continuous wavy pattern.

The bodies may be rigid, semi-rigid or flexible strips or elongated structures comprised of separate blocks, each block having two divergent sloping surfaces. Whether in strip or block form, each body may be adapted for attachment to a flexible material or fabric, such that the opposing bodies form a magnetic zipper.

The outwardly facing poles of the magnets on the first body may all be the same but opposite to the outwardly facing poles of the magnets on the second body. Alternatively, the outwardly facing poles of the magnets on both bodies may be reversed in a pattern that discourages misalignment upon closure.

The magnets may be mounted upon or embedded into the sloping surfaces the outwardly facing poles of the magnets being flush with the sloping surfaces. Alternatively, the magnets may be embedded within the bodies such that the magnets are not visible.

The magnetic closure system may further include an article of clothing such as a shirt, jacket or coat to which the bodies are attached to form a magnetic zipper structure having a top and a bottom portion. At least the bottom portion may include an extra set of magnets to assist in maintaining the magnetic zipper structure in a closed configuration.

DETAILED DESCRIPTION OF THE PREFERRED EMBODIMENTS

This invention is directed to a closure system wherein first and second opposing bodies with embedded magnets facilitate temporary attraction while allowing opening of the closure through reasonably applied manual opposed pulling. As used herein, the term "body" should be taken to include elongated strips, whether flexible, bendable, semi-rigid or rigid, as well as separate or individual units or cells that make up elongated structures. Each body has a profile (when viewed from the side) having peaks, troughs and slopes between the peaks and troughs. Permanent magnets are embedded within the slopes of the bodies, with the poles of the magnets being outwardly facing. The peaks on one side of the closure are received by the troughs of the side, such that the magnets on one side are attracted to the magnets of the other side to keep the bodies in contact until manually pulled apart.

Figure 1A:
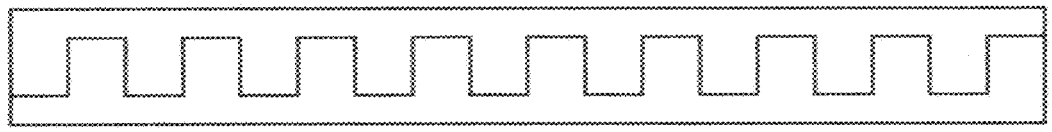
FIG. 1A is a simplified diagram that illustrates a square/rectangular interlocking system that defines a "square wave" waveform.
Figure 1B:
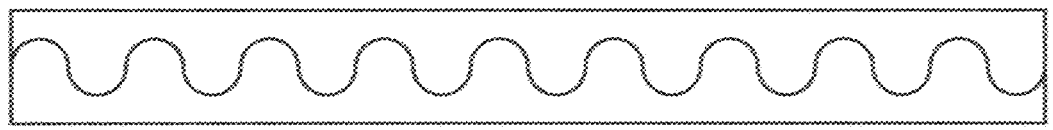
FIG. 1B is a simplified diagram that illustrates a convex-concave interlocking system that defines an wavy or undulating waveform.
Figure 1C:
FIG. 1C is a simplified diagram that illustrates a pointed interlocking system that defines an triangular waveform.
Figure 1D:
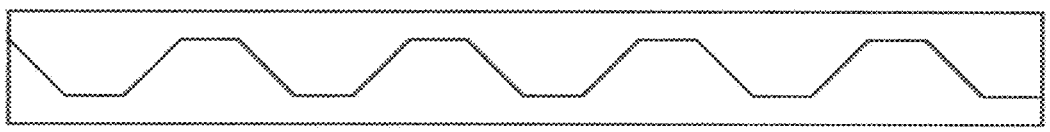
FIG. 1D is a simplified diagram that illustrates a preferred interlocking system that defines a trapezoidal waveform.

Several different edge profiles are applicable to the invention, including square/rectangular (FIG. 1A); wavy/undulating (FIG. 1B); triangular (FIG. 1C); and trapezoidal (FIG. 1D). The trapezoidal design of FIG. 1D was selected as the preferred embodiment, as it allows for three different axes of alignment unlike the other options which only have one or two. This means that closure does not require precise alignment at a perpendicular angle for closure, as with some of the other designs.

Figure 2A:
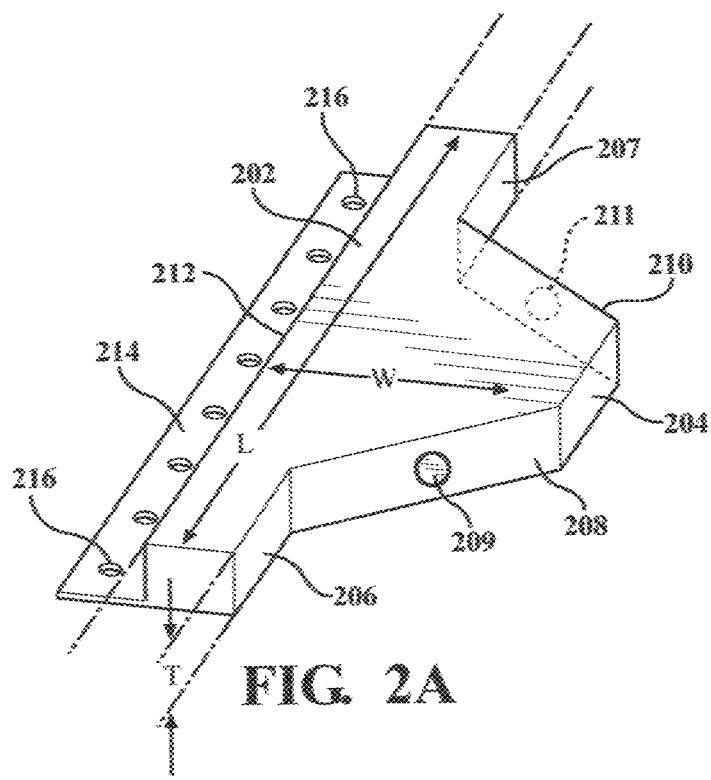
FIG. 2A is a drawing that shows a single cell design in a trapezoidal interlocking system including an offset, mirror image of the same cell pattern.
Figure 2B:
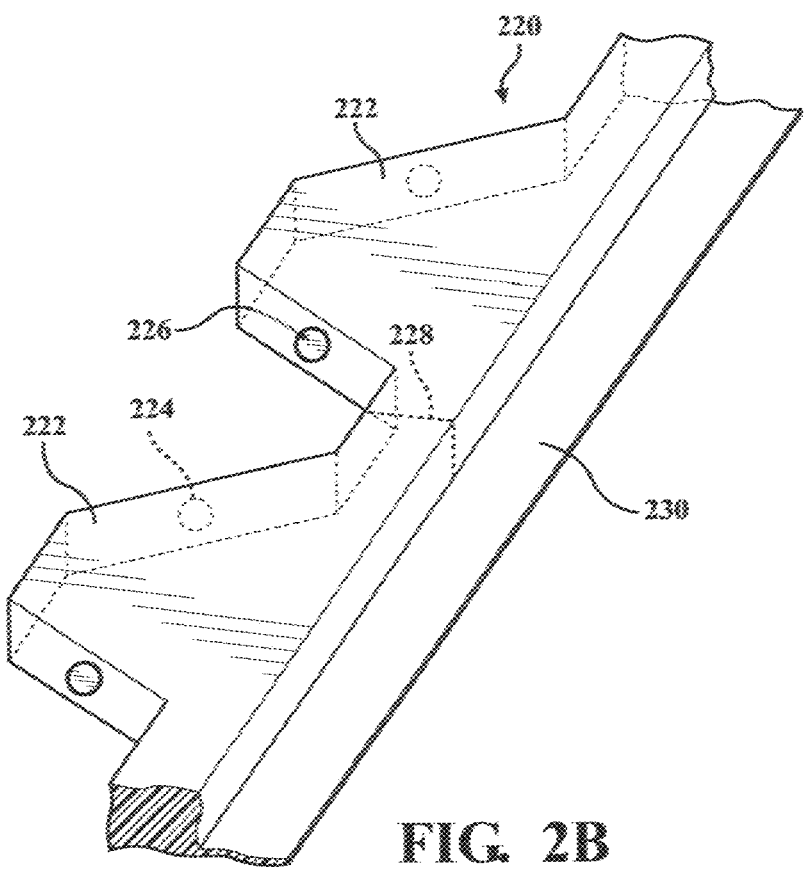
FIG. 2B illustrates how multiple cells may be integrated into a continuous strip.
Figure 3:
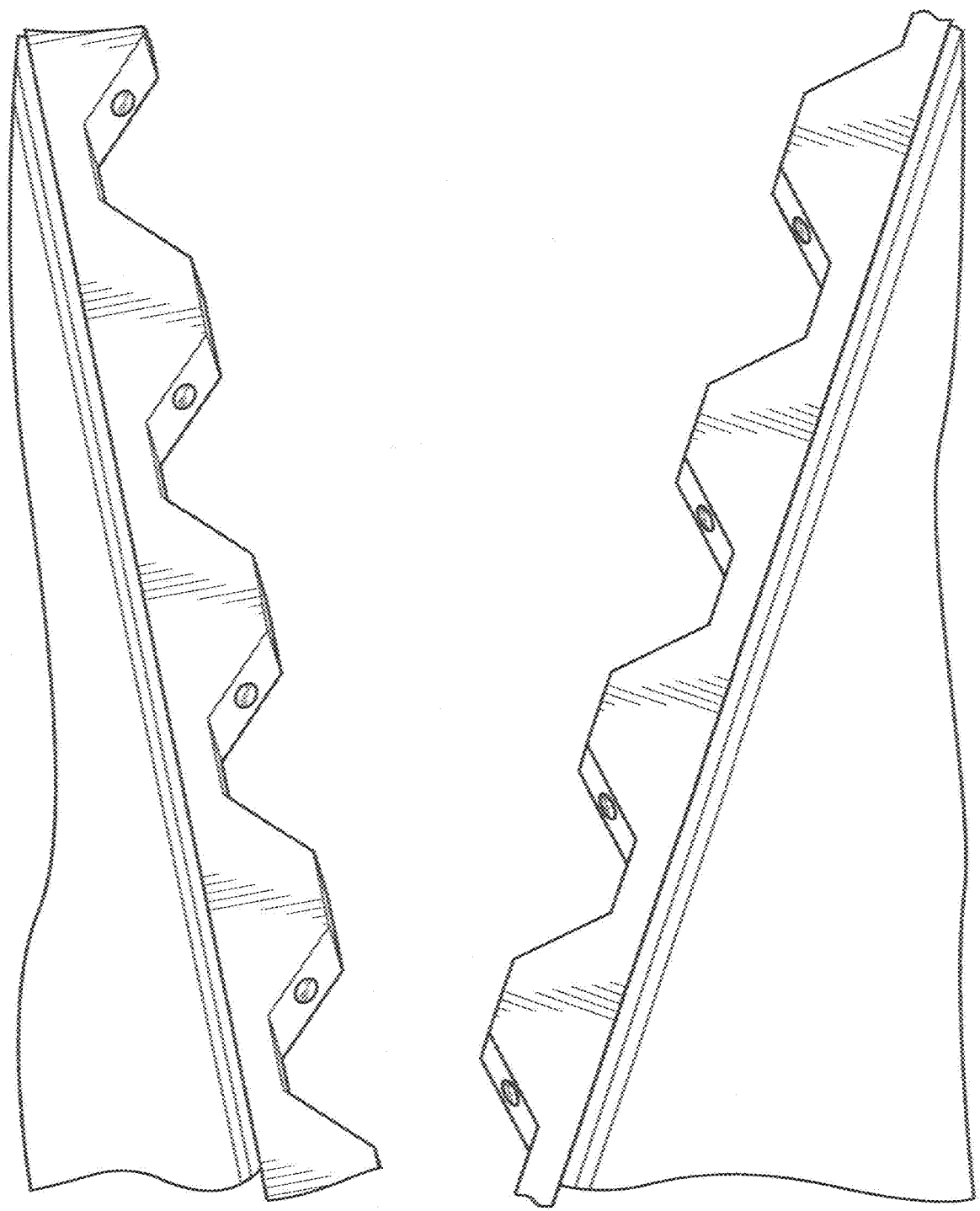
FIG. 3 is drawing that shows opposing continuous strips of cells in an open configuration.
Figure 4:
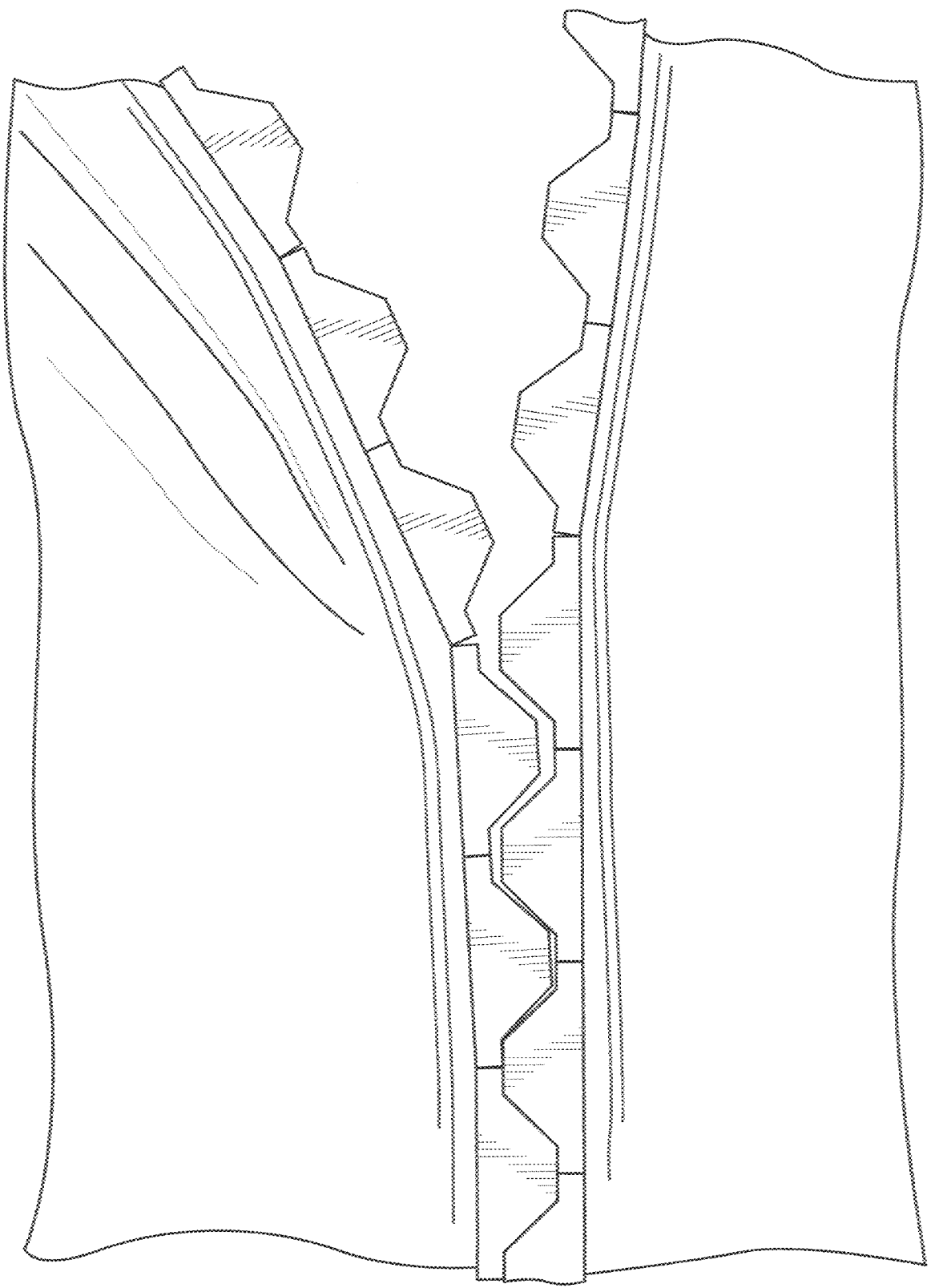
FIG. 4 is a drawing that shows individual cells in a partially open closure embodiment.

FIG. 2A shows a design cell 202 associated with a trapezoidal pattern that interlocks with an offset, mirror image composed of the same cells. As shown in FIG. 2B, multiple cells 222 may be integrated into an elongated strip 220, with dashed line 228 indicating where the pattern may be separated into the individual cells 222. The cells, or strips may be made of any suitable materials preferably plastic, though wood and even non-ferrous or non-magnetic metals such as aluminum or stainless steel may alternatively be used. If individual cells are used as shown in FIG. 4, the cells are preferably hard and/or rigid or semi-rigid, whereas if continuous strips are used as shown in FIG. 3, the strips may be manufactured in a malleable material such as neoprene or some type of rubber that better lets the apparel move freely.

Continuing the reference to FIGS. 2A, B, each unit cell of the trapezoidal design comprises a block having a length L, a width W, and a thickness T. L, W, and T can be virtually any dimension from fractions of an inch to more than an inch, depending upon the application. As one example of many, for a jacket, for example, L may be on the order of an inch, W may be on the order of 0.5 inch, and T may be 0.25 inch, more or less.

Each block has a back surface 212, a front surface 204, and intermediate surfaces 207, 207. With an elongated series of cells, the front surfaces 204 define "peaks" in the pattern, whereas the intermediate surfaces 207, 207 form "troughs." Sloping side surfaces 208, 210 extend from the intermediate surfaces 206, 207 to the front surface 204 at angles, preferably 45 degrees, though other angles may be used and, in fact, the angles of 208 and 210 may be different. Sloping side surfaces 208, 210

Magnets 209, 211, mounted or embedded in the angled sloping side surfaces 208, 210, attract (or repel) corresponding magnets such as 224, 226 in FIG. 2B. Through testing, it was determined that circular, rare-earth (N45) magnets at least 0.25" in diameter are sufficient to facilitate unassisted closure in a jacket closure system. Of course, different strength magnets could be used for different applications, and although cylindrical or puck shapes are preferred, other shapes may work as well.

Depending upon dimensional tolerances, the magnets 209, 211, 224, 226 may be press-fit or bonded into position with one pole of the magnet facing outwardly. While thinner magnets may be glued to the bodies, in the preferred embodiments larger magnets having cylindrical shapes are inserted into cavities formed in the bodies such that their outer surfaces are flush with the surrounding material comprising the cells or strips. As a further option, particularly if the closure is made as a continuous strip of flexible, resilient rubber or rubber-like material, the magnets may be entirely enclosed within the material, such that the magnets are not visible.

To fasten the magnetic structures to an article of clothing, outward tab 214 shown in FIG. 2A or tab 230 in FIG. 2B may be used. The tabs may have holes 216 for sewing or attachment purposes. Alternatively, the tabs or strip 230 of FIG. 2B may be glued, heat-bonded, or simply sewn through by machine.

Figure 5A:
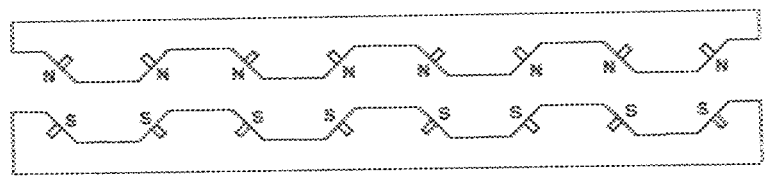
FIG. 5A is a drawing that shows outwardly facing magnets of the same polarity on opposing sides of a magnetic closure system according to the invention.
Figure 5B:
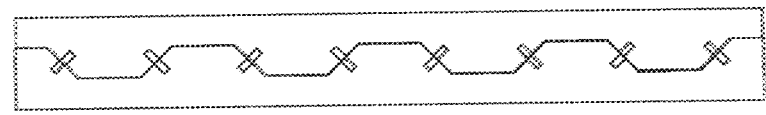
FIG. 5B shows the closure system of FIG. 5A in a desired closure pattern.
Figure 5C:
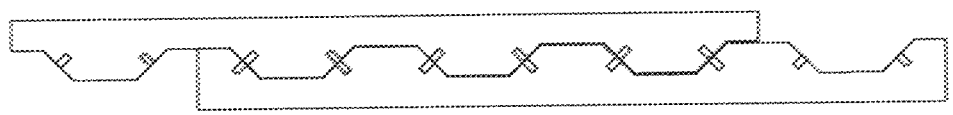
FIG. 5C shows how the closure system of FIG. 5A can also close at any peak-to-trough correspondence, including unwanted matching of immediately adjacent cells, possibly leading to an unwanted offset in a garment embodiment, for example.

The polarities of the magnets on opposing sides of the closure may be of any operative pattern. For example, as shown in FIG. 5A, all magnets on one side of the closure may have one pole facing outwardly, with the magnets on the other side of the closure having the opposite pole facing outwardly. However, this is not the preferred arrangement, since the resulting structure may close with a desired configuration (FIG. 5B), or an undesired "offset" appearance, as shown in FIG. 5C. Accordingly, the pattern may be staggered such that the north and south pole positions are reversed after 2 or more cells, so that the structure encourages proper closure; that is, instead of being "off" by 1 inch and still closing, the structure would have to be "off" by several inches to close incorrectly, which is unlikely.

Figure 5D:
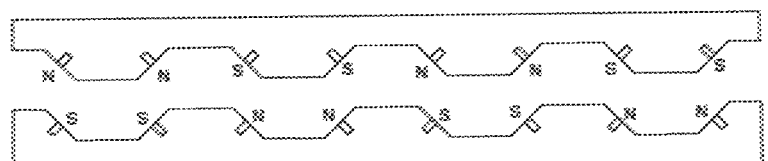
FIG. 5D is a drawing that shows how the outwardly facing magnets on both sides of a closure may be staggered to avoid adjacent cell mismatches.
Figure 5E:
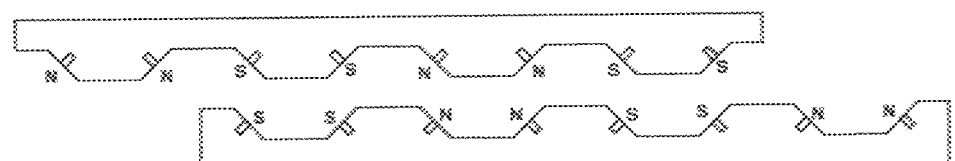
FIG. 5E shows how, if an attempt is made to close the pattern of Figure D with a one-cell offset, the magnets resist the attempt.
Figure 5F:
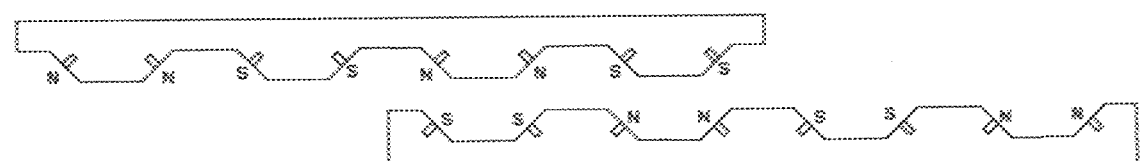
FIG. 5F show how, with the arrangement of Figure D, a lateral translation of two (or other even number) of cells must be used for closure, thereby discouraging misalignments.
Figure 5G:
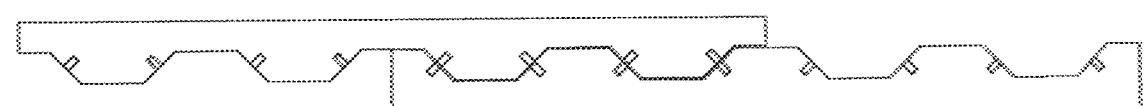
FIG. 5G illustrates the arrangement of Figure D incorrectly closed with a 2-cell offset.

FIG. 5D is a drawing that shows how the outwardly facing magnets on both sides of a closure may be reversed with every other cell such that if an attempt is made to close the pattern of Figure D, the magnets resist the attempt as shown in FIG. 5E. FIG. 5F show how, with the arrangement of Figure D, a lateral translation of two (or other even number) of cells must be used for closure, thereby discouraging misalignments. FIG. 5G illustrates the arrangement of Figure D incorrectly closed with a 2-cell offset. It will be appreciated that if pole reversals are made at even wider intervals, misalignment will be even less likely. Indeed, if pole reversals are made at irregular intervals, misalignment would be virtually impossible.

Figure 6:
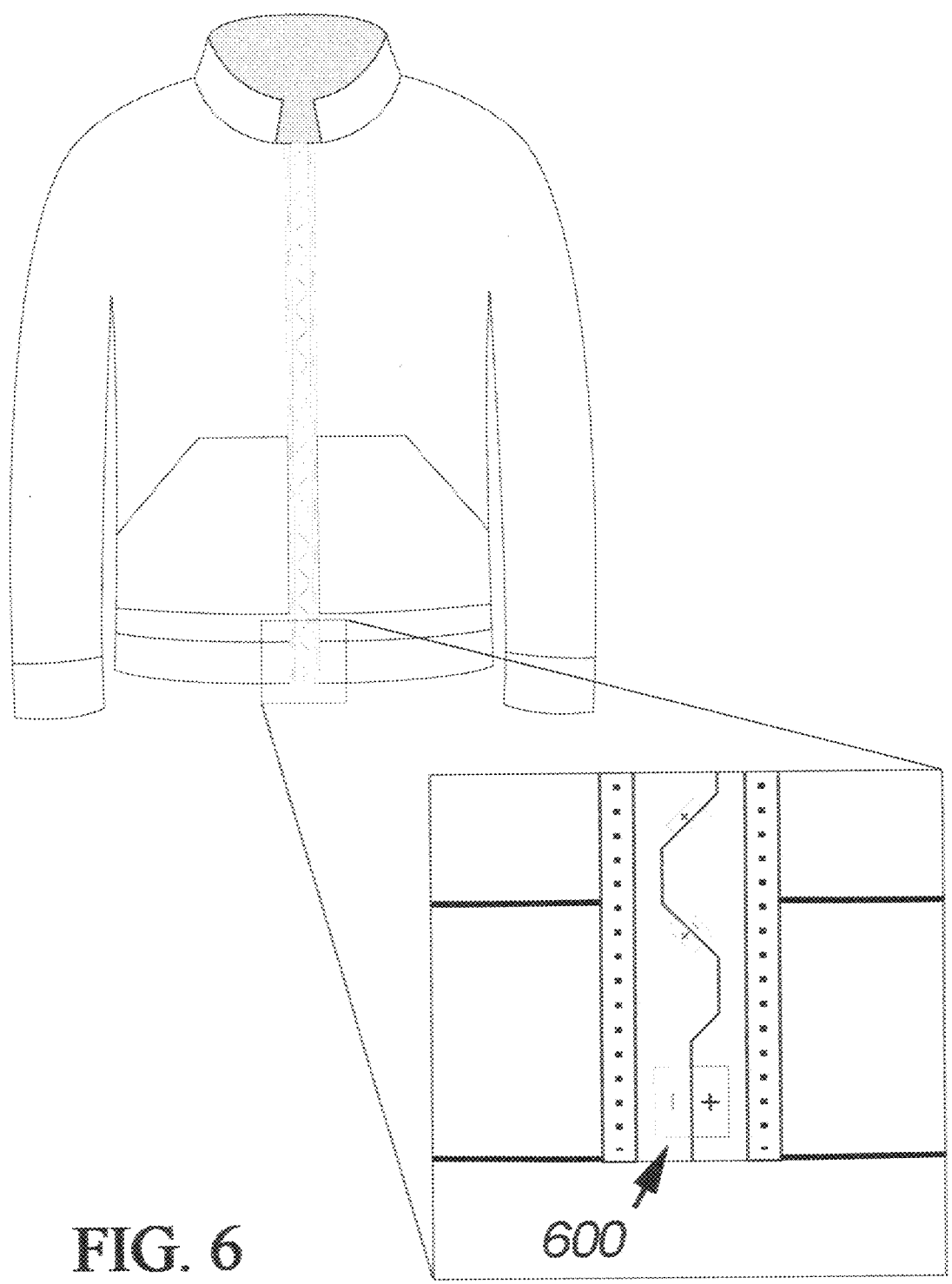
FIG. 6 is a drawing that shows how an additional pair of magnets may be used at the end of a closure, such as at the bottom of a garment such as shirt, jacket or coat.

FIG. 6 is a drawing that shows how an additional pair of magnets 600 may be used at the end of a closure, such as at the bottom of a garment such as shirt, jacket or coat.

The invention claimed is:
1. A magnetic closure system, comprising:
first and second opposing bodies;
wherein each body has a profile with peaks, troughs and side surfaces between the peaks and troughs;
wherein each side surface slopes outwardly and away from a respective one of the peaks to a respective one of the troughs;
a separate permanent magnet disposed on or in each of the sloping side surfaces of each body, with the poles of each magnet being outwardly facing; and
wherein the peaks of each body are received by the troughs of the other body, such that the magnets of one body are attracted to the magnets of the other body to keep the bodies in contact until the bodies are manually pulled apart.

2. The magnetic closure system of claim 1, wherein the peaks, troughs and sloping surfaces are flat, such that the profile of each body defines a repeating trapezoidal pattern.

3. The magnetic closure system of claim 2, wherein:
the magnets are bodies with longitudinal axes and poles at each end; and
the longitudinal axes are perpendicular to the sloping side surfaces.

4. The magnetic closure system of claim 2, wherein:
the peaks and troughs define spaced-apart parallel lines; and
the flat sloping surfaces form an angle of 45 degrees relative to the parallel lines.

5. The magnetic closure system of claim 1, wherein the peaks and troughs are pointed, such that the profile of each body defines a repeating triangular pattern.

6. The magnetic closure system of claim 1, wherein the peaks, troughs and sloping surfaces are curved and smooth, such that the profile of each body defines a continuous wavy pattern.

7. The magnetic closure system of claim 1, wherein each body includes a tab extension adapted for attachment to a flexible material or fabric, such that the opposing bodies form a magnetic zipper.

8. The magnetic closure system of claim 1, wherein the bodies are elongated strips comprised of separate blocks, each block having two divergent sloping surfaces.

9. The magnetic closure system of claim 8, wherein each block includes a tab extension adapted for attachment to a flexible material or fabric, such that the opposing blocks form a magnetic zipper.

10. The magnetic closure system of claim 8, wherein:
each trough has a length with a midpoint; and
the bodies are separated into blocks at the midpoint of each trough.

11. The magnetic closure system of claim 1, wherein the outwardly facing poles of the magnets on the first body are the same but opposite to the outwardly facing poles of the magnets on the second body.

12. The magnetic closure system of claim 1, wherein the outwardly facing poles of the magnets on both bodies form a random pattern that discourages misalignment upon closure.

13. The magnetic closure system of claim 1, wherein the bodies are rigid or semi-rigid strips.

14. The magnetic closure system of claim 1, wherein the bodies are flexible strips.

15. The magnetic closure system of claim 1, wherein the magnets are mounted upon or embedded into the sloping surfaces.

16. The magnetic closure system of claim 1, wherein the outwardly facing poles of the magnets are flush with the sloping surfaces.

17. The magnetic closure system of claim 1, wherein the magnets are embedded within the bodies such that the magnets are not visible.

18. The magnetic closure system of claim 1, wherein the peaks of the bodies are spaced apart at a distance in the range of 0.5 to 2 inches.

19. The magnetic closure system of claim 1, further including an article of clothing to which the bodies are attached to form a magnetic zipper structure.

20. The magnetic closure system of claim 19, wherein:
the article of clothing is a shirt, jacket or coat;
magnetic zipper structure has a top and a bottom portion; and
at least the bottom portion has an extra set of magnets to assist in maintaining the magnetic zipper structure in a closed configuration.

21. The magnetic closure system of claim 1, wherein:
the magnets are bodies with longitudinal axes and poles at each end; and
the longitudinal axes are perpendicular to the sloping side surfaces.

* * * * *